(12) United States Patent
Grow et al.

(10) Patent No.: US 7,475,592 B2
(45) Date of Patent: Jan. 13, 2009

(54) RHEOMETER

(75) Inventors: Andrew Grow, Mogadore, OH (US);
Henry Pawlowski, Seville, OH (US);
Keith Buzek, Akron, OH (US)

(73) Assignee: Alpha Technologies Services LCC, Akron, OH (US)

( * ) Notice: Subject to any disclaimer, the term of this patent is extended or adjusted under 35 U.S.C. 154(b) by 226 days.

(21) Appl. No.: 11/455,902

(22) Filed: Jun. 19, 2006

(65) Prior Publication Data
US 2007/0289363 A1      Dec. 20, 2007

(51) Int. Cl.
*G01N 11/10* (2006.01)
(52) U.S. Cl. .................................................. 73/54.39
(58) Field of Classification Search ............... 73/54.01, 73/54.27, 54.39, 54.37
See application file for complete search history.

(56) References Cited

U.S. PATENT DOCUMENTS

| | | | | |
|---|---|---|---|---|
| 3,382,535 A | * | 5/1968 | Ferrari | ........................ 425/461 |
| 3,387,490 A | | 6/1968 | Wise | |
| 3,479,858 A | | 11/1969 | Umeno et al. | |
| 3,535,914 A | | 10/1970 | Veith et al. | |
| 3,681,980 A | * | 8/1972 | Decker | ........................ 73/794 |
| 3,688,567 A | | 9/1972 | Karper et al. | |
| 3,720,099 A | | 3/1973 | Wolff et al. | |
| 4,337,646 A | | 7/1982 | Fraleigh | |
| 4,343,190 A | | 8/1982 | Danko et al. | |
| 4,552,025 A | | 11/1985 | Barker et al. | |
| 4,577,412 A | * | 3/1986 | McKinney | .................... 33/701 |
| 4,624,132 A | * | 11/1986 | Parnaby et al. | ............. 73/54.09 |
| 4,829,830 A | | 5/1989 | Tosaki | |
| 4,948,545 A | * | 8/1990 | Bashir et al. | ............. 264/210.8 |
| 4,953,406 A | | 9/1990 | Putman | |
| 5,079,956 A | * | 1/1992 | Burhin et al. | ................. 73/846 |
| 5,163,317 A | | 11/1992 | Ono et al. | |
| 5,271,266 A | | 12/1993 | Eschbach | |
| 5,311,767 A | * | 5/1994 | Mathews et al. | .............. 73/843 |
| 5,357,783 A | | 10/1994 | Eschbach | |
| 5,526,693 A | | 6/1996 | Wise | |

(Continued)

FOREIGN PATENT DOCUMENTS

EP         0466060 A        1/1992

OTHER PUBLICATIONS

"Inivitation to Pay Additional Fees" from corresponding PCT application US2007/014279 mailed Dec. 4, 2007, 4 pps.

(Continued)

*Primary Examiner*—John Fitzgerald
(74) *Attorney, Agent, or Firm*—Wolf, Greenfield & Sacks, P.C.

(57) ABSTRACT

A rheometer die with a groove configuration for reducing sample slippage in a rheometer chamber is provided. The rheometer die includes a surface and at least one radial groove extending into the surface. The groove defines at least a portion of a sample-holding chamber constructed to hold a sample. The groove may include a first zone and a second zone with a transition zone therebetween. The groove may also include a substantially wedge-shaped portion with sidewalls which taper generally towards the center of the rheometer die such that imaginary extensions of the sidewalls intersect before reaching the center of the die. A plurality of grooves may extend into the rheometer die. The rheometer die may be incorporated into a rheometer for testing process characteristics of a material.

46 Claims, 6 Drawing Sheets

U.S. PATENT DOCUMENTS

| | | |
|---|---|---|
| 5,597,958 A | 1/1997 | Wise |
| 5,610,325 A | 3/1997 | Rajagopal et al. |
| 5,631,409 A | 5/1997 | Rajagopal et al. |
| 6,164,818 A | 12/2000 | Dick et al. |
| 6,336,357 B1 | 1/2002 | Pawlowski et al. |
| 6,523,397 B1 | 2/2003 | Tosaki |

OTHER PUBLICATIONS

Pawlowski & Wyszynski "Measurement of Thermoplastic Polymer Melt Viscosity and Transitions using a DMA with a Sealed and Pressurized Sample Chamber" Presented at Antec, May 2, 2005, 13 pgs.

Pawlowski et al. "Measurement of the Viscoelastic Properties of Elastomers with a new Dynamic Mechanical Rheological Tester" presented at Belgian Plastics & Rubber Institute, Leuven, Belgium Apr. 19, 1994., 43 pgs.

ASTM D-2084 Standard Test Method for Rubber Property—Vulcanization Using Oscillating Disk Cure Meter, 4 pgs.

"International Search Report and Written Opinion" from corresponding PCT application US2007/014279 mailed Feb. 29, 2008, 16 pps.

* cited by examiner

PRIOR ART

RHEOMETER

FIELD

Aspects of the present invention relate generally to a rheometer, and more particularly to a rheometer die with a groove configuration for reducing slippage of a material sample within a rheometer chamber.

DISCUSSION OF RELATED ART

Various types of rheometers exist to test the process characteristics of materials, such as rubber, vulcanized rubbers, polymers, plastics, thermoplastics, and other materials. In a typical rheometer, a material sample is placed within a chamber defined between two rheometer dies. A strain is applied to the sample on one side of the sample and a measuring device is provided on the other side to measure the torque on the sample. For example, one rheometer die may oscillate relative to a stationary rheometer die to create a rotary shear force on the sample. A torque transducer may be mounted on the stationary die to measure the torque on the sample which indicates the response of the sample to the shear force. In some rheometers, a disk may be placed within the test chamber. In these rheometers, the disk inside of the test chamber may be rotated or oscillated to impart the torque on the sample.

During the process of testing a process characteristic of a material sample with a rheometer, the sample is typically heated above its melting point and then cooled. As the material is cooled from a molten state to a solid state, the sample may shrink within the chamber. This shrinking may cause the sample to pull away and slip from the surfaces of the rheometer die. Once the sample slips from the surface of a rheometer die, the measured torque values become less accurate and may produce inaccurate data. Rheometers may also be used to test samples that solidify upon curing of the sample.

There have been several attempts to prevent slippage of the material sample from a rheometer die as the sample solidifies within a rheometer chamber. For example, according to one approach, a crosshatch pattern is formed into the die surface in an effort to better grip the sample.

Figure 1:
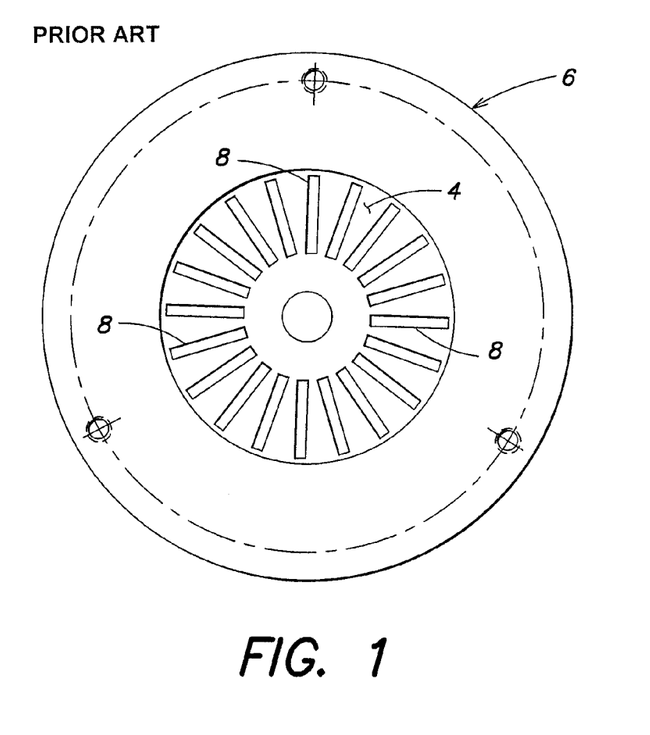
FIG. 1 is a top view of a conventional rheometer die.

According to another approach to prevent sample slippage, a plurality of grooves are formed into a rheometer die surface. For example, as illustrated in FIG. 1, a rheometer die 6 has a plurality of grooves 8 extending into the surface 4 of the die 6. These grooves 8 are arranged in a radial pattern about the center of the die 6 and are substantially rectangular-shaped. Although these grooves 8 may help to reduce slippage of a sample within a rheometer chamber, the sample still shrinks away from the grooved walls and slippage of the sample still occurs as the sample solidifies in the chamber.

SUMMARY

In one illustrative embodiment, a rheometer die is provided. The rheometer die comprises a surface having a center and at least one radial groove extending into the surface. The at least one groove defines at least a portion of a sample-holding chamber constructed and arranged to hold a sample. The at least one groove also defines a first zone having sidewalls which taper generally towards the center of the die, and a second zone with sidewalls which also taper generally towards the center of the die. The sidewalls of the first and second zones define a transition region between the first zone and the second zone, and at least one of the sidewalls have a non-linear portion defining the transition region.

In another illustrative embodiment, a rheometer die is provided. The rheometer die comprises a surface having a center and at least one radial groove extending into the surface. The at least one groove defines at least a portion of a sample-holding chamber constructed and arranged to hold a sample. The at least one groove also defines a first zone constructed and arranged to wedge a sample in the groove as the sample shrinks within the chamber upon cooling of the sample from a molten state to a solid state. The at least one groove also includes a second zone constructed and arranged such that as the sample shrinks, at least a portion of the sample located in the first zone moves into the second zone. The first and second zones define a transition region therebetween, where the transition region includes an expansion area to accommodate movement of the sample into the second zone as the sample shrinks.

In a further illustrative embodiment, a rheometer die is provided. The rheometer die comprises a surface having a center and at least one radial groove extending into the surface. The at least one groove defines at least a portion of a sample-holding chamber constructed and arranged to hold a sample. The at least one groove defines a substantially wedge-shaped portion, where the wedge-shaped portion has sidewalls which taper generally towards the center of the die such that imaginary extensions of the sidewalls intersect before reaching the center of the die.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF DRAWINGS

Various embodiments of the invention will now be described, by way of example, with reference to the accompanying drawings, in which.

DETAILED DESCRIPTION

Rheometers are typically used to determine various properties of a viscoelastic material, such as rubber, vulcanized rubbers, polymers, plastics, thermoplastics, or other material. These instruments may be commonly referred to as Moving Die Rheometers (MDR), Rubber Process Analyzers (RPA), Oscillating Disk Rheometers (OCD) and/or Mooney Viscometers. These instruments may apply a rotational shear force to a material sample and may measure the resulting torque on the sample. Information about the material may be derived from the measured torque on the sample. The material sample to be tested may be enclosed within a chamber formed between two opposing rheometer dies and the rotational shear force may be applied to the material sample by rotating one die while the other die remains stationary. It should be appreciated that the term "rheometer" refers to any Theological instrument used to measure a process characteristic of a viscoelastic material, including, but not limited to, the devices listed above.

As discussed above, a rheometer may be configured with dies forming the upper and lower portions of the test chamber. In addition, the rheometer may be configured with a disk disposed within the test chamber. Therefore, for purposes of describing and claiming the present invention, the term "rheometer die" or "die" is intended to broadly encompass any suitable testing element such as dies (upper and/or lower portions of the test chamber) and disks (elements placed within the test chamber), as the invention is not limited in this respect. In this regard, the term "rheometer die" and "die" means a testing element which is adapted to form an outer portion of the chamber, a testing element which is adapted to be placed in the chamber, or any other suitable testing element cooperating with the rheometer to test a sample, as the present invention is not limited in this respect.

Aspects of the invention are directed to a rheometer die which is configured to reduce and/or eliminate the amount of sample slippage which may occur within the rheometer test chamber. Sample slippage may occur when a sample solidifies and shrinks within the rheometer test chamber. Sample solidification may result when a molten sample cools to a solid form and/or when a sample cures due to a chemical reaction occurring within a sample. When sample slippage is reduced and/or eliminated, the measured torque under higher strains may be accurate and repeatable. This may be in contrast to other types of rheometers, where the material sample may slip away from the rheometer die under high strains, such that the measured torque may not provide an accurate torque measurement.

In one embodiment, a rheometer die may be circular shaped and one or more grooves may extend into a surface on the rheometer die to prevent slippage of the sample away from the rheometer die as the sample solidifies. In one embodiment, these grooves may be arranged in a "spoke-like" pattern radially extending about the center of the rheometer die.

Conforming the sample to a die may produce more accurate torque measurements. As mentioned above, sample shrinkage within the die may produce inaccurate measurements. Therefore, according to an aspect of the invention, it is desirable to hold the sample more tightly such that slippage is minimized. This may be accomplished in a variety of ways and in one aspect, this is accomplished by controlling the shrinkage of the material in the die, whereby any resulting space between the sample and sample chamber as the sample cools is minimized or at least limited to those areas where sample slippage can be tolerated.

In one aspect, a rheometer die includes a dual-zone sample chamber. The rheometer die includes a surface with at least one groove extending into the surface, and the groove includes two zones. A first zone may have sidewalls that taper towards the center of the die, and a second zone may also have sidewalls which taper towards the center of the die. The first and second zones may define a transition region between the two zones which may include a non-linear portion defining the transition region.

In another aspect, a first zone of a groove in the rheometer die surface may be constructed to wedge a sample in the groove as the sample shrinks. A second zone in the groove may be constructed such that as the sample shrinks, at least a portion of the sample located in the first zone moves into the second zone. The first and second zones may define a transition region therebetween, which includes an expansion area to accommodate movement of the sample into the second zone as the sample shrinks. However, it is to be appreciated that a groove having two zones is not required for each embodiment of the rheometer die.

In yet another aspect, a rheometer die includes a surface with at least one groove extending into the surface. The groove may have a substantially wedge-shaped portion, with sidewalls which taper generally towards the center of the die but do not intersect at the center of the die. In one embodiment, imaginary extensions of the sidewalls intersect before reaching the center of the die. However, it is to be appreciated that a groove having sidewalls with this over center configuration is not required for each embodiment of the rheometer die.

As discussed above, various types of rheometers exist to test viscoelastic properties of a material, such as a rubber, plastic, polymer or other elastomer. It should be appreciated that the rheometer die of the present invention may be used with any suitable rheometer, as the present invention is not limited in this respect.

Figure 2:
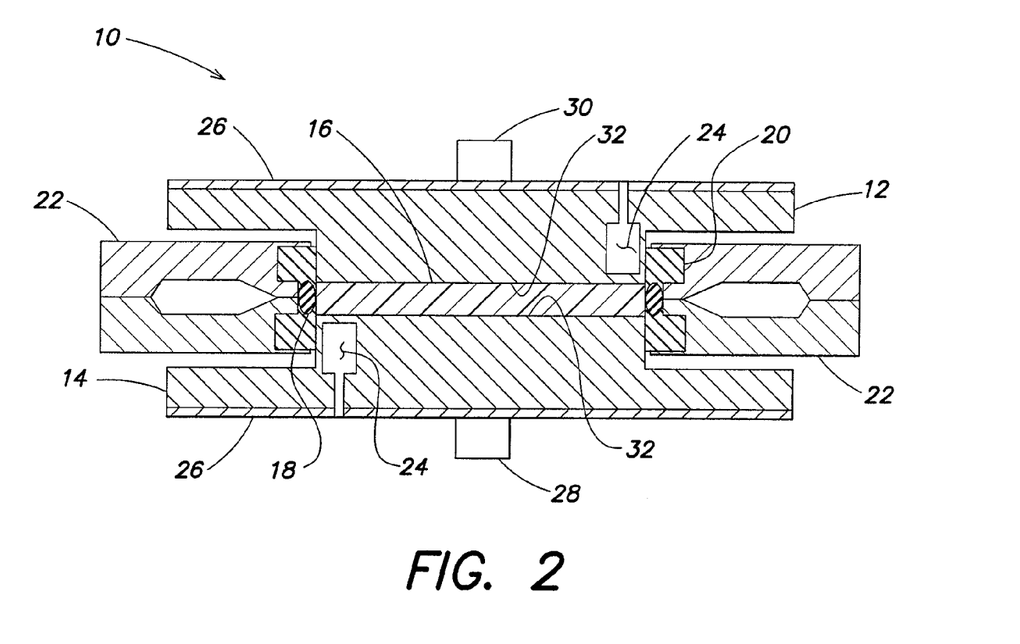
FIG. 2 is a cross-sectional view of an exemplary rheometer according to one illustrative embodiment.

Turning now to the Figures, and in particular to FIG. 2, a portion of an exemplary rheometer 10 is illustrated. This particular rheometer 10 includes an upper die 12 and a lower die 14 which define a chamber for holding a material sample 16. The rheometer may include plates 22 and one or more seals 20 and/or O-rings 18 positioned around the chamber to seal the material sample 16 within the chamber.

As mentioned above, under certain rheometer test conditions, the sample 16 may be heated. In one embodiment, the sample 16 is heated to test the process characteristics of the sample material at certain temperatures and/or at certain temperature ranges. In one embodiment, the rheometer may be used to test process characteristics of a material as it transitions from a molten state to a solid state. In another embodiment, the sample 16 may be heated to soften and/or melt the sample so that the sample may conform to the contours of the rheometer chamber.

In the illustrative embodiment of FIG. 2, heaters 26 are provided on each rheometer die 12, 14 to selectively increase the temperature of the sample 16. It should be appreciated that a heater may be provided on one or more of the rheometer dies 12, 14. Temperature sensors 24 may also be provided to measure and assist in controlling the temperature of the sample. As shown in FIG. 2, a temperature sensor 24 may be provided on one or more rheometer dies 12, 14. The sensor 24 may be positioned closer to the surface 32 of the die which contacts the sample to more accurately measure the temperature of the sample 16.

In one embodiment, the rheometer is temperature controlled. In this respect, various tests may be conducted on the sample at any desired temperature or temperature range. In one embodiment, a cooling system, such as a forced air system may be incorporated into the rheometer to cool the sample.

Other suitable environmental controls may be employed, as the invention is not limited in this regard. Indeed, no environmental controls need be employed.

To impart a shear force into the material sample 16, one die 14 may move relative to the other die 12. In the illustrative embodiment of FIG. 2, the upper die 12 is stationary, while the lower die 14 is coupled to a drive mechanism for rotation. It should be appreciated that in other embodiments, the upper die 12 may be configured for movement while the lower die 14 may be stationary, as the present invention is not limited in this respect. As shown in FIG. 2, a shaft 28 may couple the lower die 14 to a drive mechanism (not shown) to impart movement of the lower die 14. It should be appreciated that various components may be used to generate movement of one die, as the present invention is not so limited. The applied rotational shear force created by the moving die 14 may be oscillatory or continuous.

To measure the torque on the material sample 16, the rheometer 10 is provided with a torque transducer 30. In the illustrative embodiment of FIG. 2, the torque transducer 30 is coupled to the stationary upper die 14. In another embodiment, the torque transducer may be coupled to the moving die 12, as the present invention is not so limited. It should be appreciated that various types of torque transducers 30 or other suitable devices and/or arrangements may be used to measure the torque on the sample 16, as the present invention is not limited in this respect.

Figures 3, 4, 5:
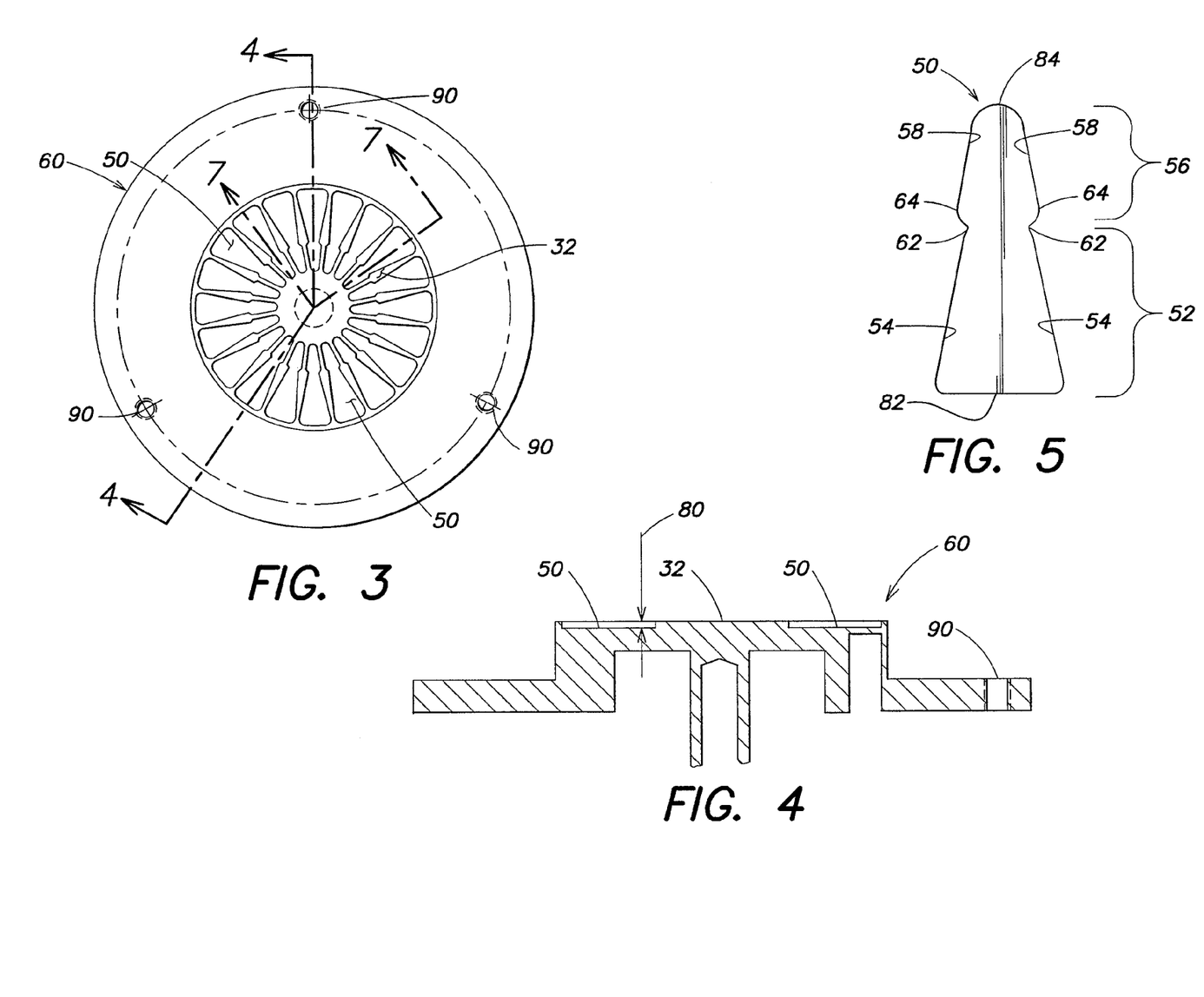
FIG. 3 is a top view of a rheometer die according to one illustrative embodiment.
FIG. 4 is a cross-sectional view of the rheometer die taken along the line 4-4 in FIG. 3 according to one illustrative embodiment.
FIG. 5 is a schematic top view of a groove of the rheometer die of FIG. 3 according to one illustrative embodiment.

Furthermore, additional components may be added to the rheometer 10. As illustrated in FIG. 4, one or more holes 90 may be drilled into and/or through a rheometer die to couple the die to other components of a rheometer. In one embodiment, actuators may be provided to automate different features of the rheometer 10. Examples of types of rheometers with various components are described in U.S. Pat. No. 6,164,818, which is hereby incorporated by reference in its entirety.

The rheometer 10 illustrated in the embodiment of FIG. 2 may operate by first moving the rheometer dies 12, 14 to an open position so that the material sample 16 may be placed between the dies 12, 14. Thereafter, the two dies 12, 14 may be moved to a closed position to form a sealed test chamber such that the sample may not leak out of the chamber. According to another embodiment, the sample may be injected into the rheometer. The chamber may have a predetermined shape and volume. The pressure within the test chamber may be maintained at a predetermined pressure.

As discussed above, the material sample 16 may be heated so that the sample conforms to the rheometer dies. The sample may also be heated to test various process characteristics of the material at certain temperatures. Heaters 26 and temperature sensors 24 may be provided to control the temperature of the sample. When the chamber is closed, the sample 16 may be subjected to an oscillating (sinusoidal) rotary shear force by movement of one die 14 relative to the other die 12. The resulting torque on the sample 16 may be measured with the torque transducer 30. In particular, the torque measurements may be a measure of the torque required to apply the shear force, or the torque induced in the stationary die 14 when the driven die 12 is rotated. In general, the softer the material, the lower the torque on the sample. However, as a sample cools from a molten state to a solid state, the harder samples increases the measured torque.

The measured resulting torque on the sample 16 may be an indication of the particular response of the sample material 16 to the particular applied shear force. Process characteristics of the sample material may be derived from the measured torque. For example, the elastic torque, viscous torque, complex torque and the modulus of the sample material may be determined based upon calculations with the measured torque on the sample. Any suitable methodology may be employed, and thus are not described in detail in the present application.

In another embodiment, the cure properties for a particular sample material may be measured with the rheometer. Even though the sample material may not be solidifying as a result of a temperature change, shrinkage of the sample may still occur during a cure test due to the chemical reactions of the sample.

As mentioned above, a shear force may be applied to the material sample 16 by rotation of one die 14 relative to the other die 12. The shear force (e.g. for imparting strain) may have a predetermined amplitude and frequency. According to one embodiment, the applied shear force is at least one amplitude of oscillation, within a range of approximately +/−0.1° arc to +/−360° arc, with a frequency of oscillation within a range of approximately 0.001 Hz to 33 Hz. However, it should be appreciated that the present invention is not limited to the application of a particular type of shear force on the material sample. It is contemplated that other amplitude and frequency ranges may be utilized, as the present invention is not so limited.

Process characteristics of a material may change significantly by varying temperature, frequency and/or strain. Testing at several different frequencies, strains and temperatures may be necessary to adequately characterize a material sample. In one embodiment, the desired frequency, strain, and temperature for a particular test may be programmed into a computer which interfaces with the rheometer.

Turning now to FIGS. 3-5, one illustrative embodiment of the die of the present invention will now be more fully described, whereby the die is constructed and arranged to hold the sample such that more accurate measurements may be obtained. In one embodiment, the rheometer die 60 has a substantially circular disk-shape. As shown in the cross-sectional view of FIG. 4, the rheometer die 60 has a substantially planar plate-like configuration. However, as discussed below, the rheometer die 60 may be shaped in other configurations, as the present invention is not limited in this respect.

In one illustrative embodiment, at least one radial groove 50 extends into a surface 32 of the rheometer die 60 which contacts the material sample. As shown, a plurality of grooves 50 may extend radially about the center of the die 60. In this particular embodiment, each groove 50 includes two zones. A first zone 52 is provided with sidewalls 54 which taper generally towards the center of the die 60, and a second zone 56 is provided also with sidewalls 58 which taper generally towards the center of the die 60. In the illustrative embodiment of FIG. 3, the second zone 56 is positioned closer to the center of the die 60, while the first zone 52 is positioned closer to the outer periphery of the die 60.

In one illustrative embodiment, a transition region 62 is defined between the first and second zones 52, 56 of the groove 50. At least one of the sidewalls may have a non-linear portion which defines the transition region 62. In the embodiment illustrated in FIGS. 3 and 5, two opposing sidewalls of the groove 50 have a non-linear portion defining the transition region 62 on each side of the groove 50. In the embodiment shown, as will be described below, the non-linear sidewall is formed as a curve, although other suitable transition regions may be employed, as the present invention is not limited in this regard. As shown in the illustrative embodiment of FIG. 3, the first zone 52 may be larger than the second zone 56. In one embodiment, the first zone 52 is substantially larger than the second zone 56. For example, in one embodiment, the radial length of the first zone 52 ranges from approximately 0.3-0.4 inches, and the radial length of the second zone 56 ranges from approximately 0.1-0.2 inches. However, in other embodiments, the size of the two zones may vary as the present invention is not so limited.

It should be appreciated that although the embodiment illustrated in FIGS. 3 and 5 features a rounded transition region 62 with a bottleneck configuration, in other embodiments, the transition region 62 may be configured differently, as the present invention is not limited in this respect. In one embodiment, the transition region includes a portion having a radius of curvature of approximately 0.03 inches. In another embodiment, the transition region 62 may only include a slight bent or angled sidewall which joins the sidewalls in one zone to the sidewalls in the other zone.

As the temperature of the sample material 16 cools so that the sample transitions into a solid state, the sample may shrink. The amount of shrinkage in the sample may be dependent upon certain parameters, for example, the coefficient of linear thermal expansion for the sample material. As shown in FIGS. 2-4, the chamber includes a sample-contacting surface 32 on the rheometer dies. The shrinkage of the sample may cause the sample to pull away from the rheometer die surfaces 32 which may alter the measured torque.

Figure 10:
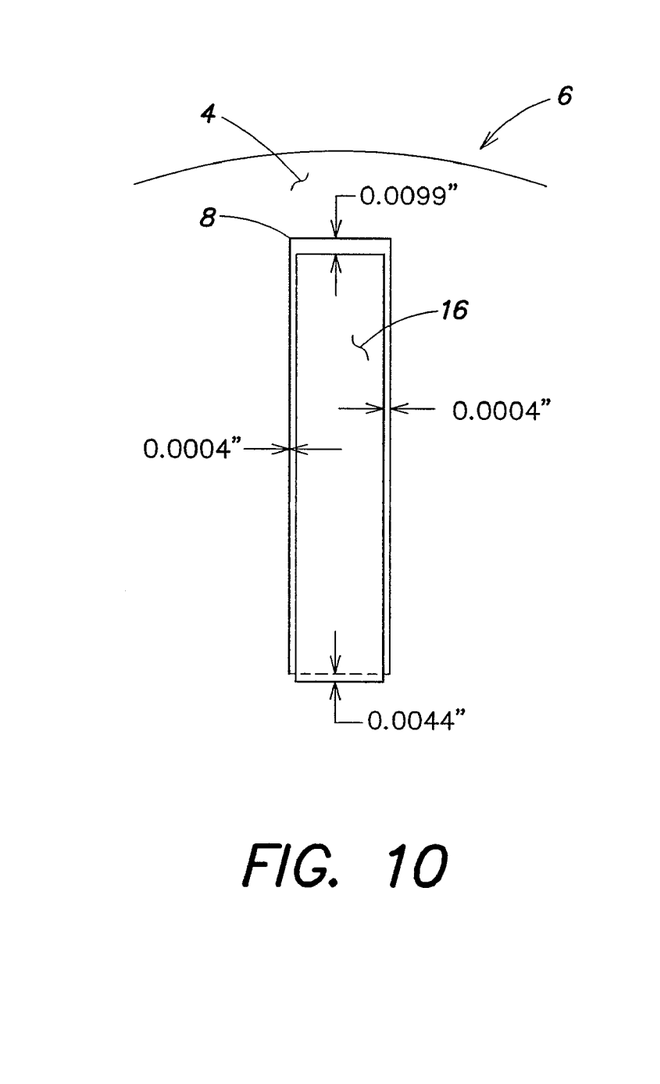
FIG. 10 is a schematic top view illustrating sample shrinkage in a groove of the rheometer die of FIG. 1.

Shrinkage of the material sample within the rheometer may occur radially and/or circumferentially. An example of material shrinkage is shown in FIG. 10. The groove 8 illustrated in this embodiment, is similar to the groove illustrated in FIG. 1. As shown, the radial shrinkage of the material sample 16 is approximately 0.0099 inches along the outer portion of the groove 8. Along the inner portion of the groove 8, the sample 16 would push inwardly due to the rotation of the die, causing an interference fit of approximately 0.0044 inches as shown in the schematic representation of FIG. 10. Radial shrinkage may be undesirable because it may affect the amount of torque transmitted through the sample. Circumferential shrinkage of the sample 16 illustrated in FIG. 10 is approximately 0.0004 inches on each side of the groove 8. Although this amount of radial shrinkage may be small, this shrinkage may allow the sample to slip due to the rotation of one of the rheometer dies. This sample slippage may produce inaccurate and non-repeatable results.

Aspects of the present invention are directed at a groove configuration on a rheometer die which reduces the amount and/or impact of the shrinkage (such as radial and/or circumferential shrinkage) of the sample. Although shrinkage may be small, it may still cause sample slippage due to the rotation of the die. Once the sample pulls away from the surfaces 32, the measured torque data may not be accurate, repeatable, or provide useful data.

The rheometer die 60 itself may also shrink as the overall temperature of the rheometer is lowered to cool the sample. The rheometer die 60 may shrink at a rate dependent upon certain parameters, for example, the coefficient of linear thermal expansion for the rheometer die material. However, the rheometer dies may be made of a material with a coefficient of linear thermal expansion that it less than the sample material. Therefore, even if the rheometer die 60 shrinks during the cooling process, the sample may shrink more, which may still cause the sample to pull away from the rheometer die surfaces. For example, in one embodiment, a polypropylene material sample is tested in a steel rheometer die chamber which is configured with a groove arrangement similar to the conventional groove arrangement depicted in FIG. 1. When the polypropylene is heated to approximately 205° C. to form a molten state and is thereafter cooled to approximately 80° C., the polypropylene material sample shrinks. Because the shrinkage of the polypropylene material sample is greater than the shrinkage of the steel rheometer die, the sample pulls away from the rheometer die surfaces. This may cause the torque transducer 30 to produce erroneous measured torque results for the polypropylene sample.

Figure 6:
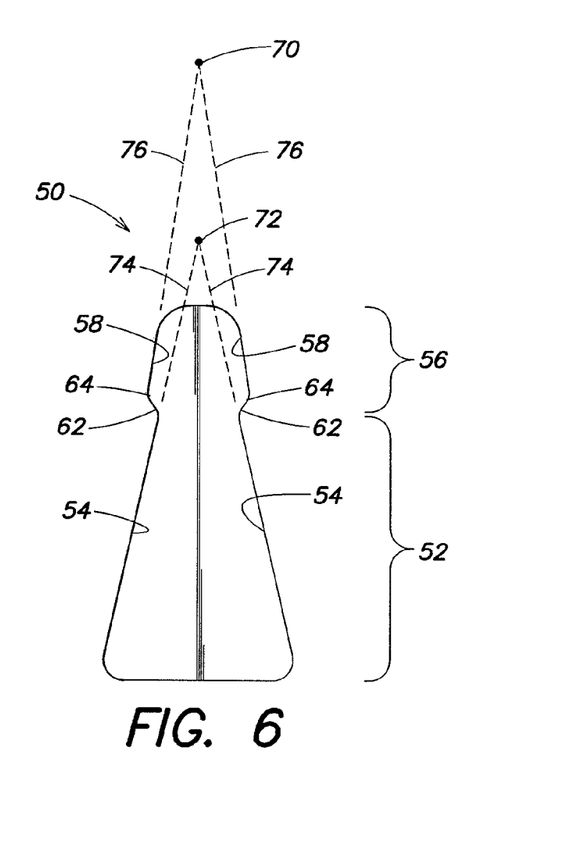
FIG. 6 is a schematic top view of a groove of the rheometer according to another illustrative embodiment.

According to one embodiment, the dual-zone groove configuration illustrated in FIGS. 3, 5 and 6, may reduce and/or prevent slippage of a material sample in a rheometer. In one embodiment, the dual-zone groove configuration may act to wedge the sample into the groove to prevent the sample from slipping away from the rheometer surfaces 32. In this respect, the groove 50 may assist in the transmission of torque through the sample to the torque transducer because the groove 50 maintains contact with the material sample.

In one embodiment, the groove 50 is shaped such that as the material sample shrinks during a cooling process, the material sample locks tighter into the die groove 50. This may allow the capture of meaningful torque data at lower temperatures. In contrast, the measured torque data at lower temperatures for prior rheometer dies is often not valuable because at low temperatures, the sample slips away from the rheometer die surfaces 32.

Figure 11:
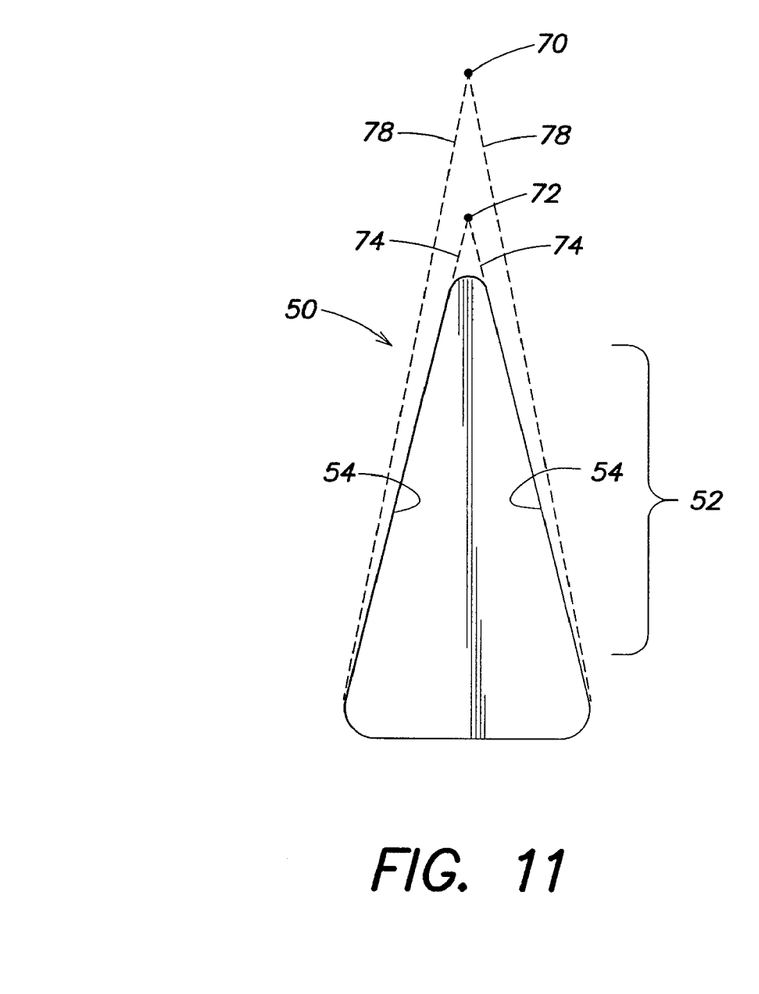
FIG. 11 is a schematic top view of a groove of the rheometer die according to another illustrative embodiment.

As shown in greater detail in the embodiments illustrated in FIGS. 6 and 11, in one embodiment, the groove 50 includes a zone 52 which defines a substantially wedge-shaped portion having sidewalls 54 which taper generally towards the center 70 of the die 60 such that imaginary extensions 74 of the sidewalls 54 intersect before reaching the center 60 of the die. As illustrated in the embodiments of FIGS. 6 and 11, these imaginary extensions 74 intersect at point 72, which is over center, such that the imaginary extensions intersect before reaching the center 70 of the die 60. By contrast, in FIG. 11, dashed lines 78 illustrate a groove configuration having converging sidewalls which intersect at the center 70 of the die 60. In one embodiment, with a groove having tapered sidewalls which converge in an over center configuration, the material sample may tighten circumferentially as the sample shrinks radially. This tightening action may help to prevent the material from pulling away from the rheometer surface 32 in areas where shrinkage away from the die would otherwise be detrimental to obtaining accurate measurements.

Also as illustrated in FIG. 6, in one embodiment, the groove 50 includes zone 56 which defines an expansion portion adjacent the wedge-shaped portion, where the expansion portion has sidewalls 58 which converge towards the center 70 of the die. In the illustrative embodiment of FIG. 6, the expansion portion is constructed such that imaginary extensions 76 of the expansion portion sidewalls 58 intersect substantially at the center 70 of the die. In one embodiment, with a groove having tapered sidewalls with imaginary extensions which converge at the center 70 of the die, circumferential shrinkage of the sample may be reduced.

In one illustrative embodiment, a groove has a first zone 52 which may serve two primary purposes. First, when this zone 52 is positioned on an outer portion of the die, the first zone 52 is configured for torque transmission. Second, when the first zone 52 is constructed with an over center configuration, the sample may tighten in the die allowing the sample to transmit more torque with less sample slippage. In one embodiment, the first zone 52 wedges a sample in the groove as the sample shrinks within the chamber upon cooling of the sample from a molten state to a solid state.

In one illustrative embodiment, the groove has a second zone 56 which may serve several primary purposes. First, as the sample shrinks, at least a portion of the sample located in the first zone 52 may moves into the second zone 56. The second zone 56 may be configured such that the crush zone (i.e. innermost portion of the groove) is close to the center of the rheometer die. The crush zone may hinder the flow of material toward the center of the die and may hinder the tightening of the sample in the groove. However, by placing the crush zone closer to the center, the undesirable effects are minimized. Second, the zone sidewalls 58 converge towards the center such that imaginary extensions converge at the center 70 of the die. This configuration may allow the sample in the second zone 56 to move further towards the center 70 of the die as it shrinks without loosening or tightening. This movement of sample in the second zone 56 allows the sample within the first zone 52 to move into the second zone 56. Third, the transition region 62 between the first and second zone may include an expansion area 64 to accommodate movement of the sample into the second zone 56 as the sample shrinks. The expansion areas 64 may be desirable such that excess material, such as semi-molten material sample may flow into the second zone 56 to give the sample in the first zone 52 more area to move. Thus, configuring the second zone 56 in a manner which allows sample in the first zone 52 to move into the second zone 56 may assist to tighten and/or wedge the sample into the groove 50 to prevent sample slippage.

It should be appreciated that the invention is not limited in this regard as one or any combination of these listed purposes may be obtained and that the invention is not limited to a die that achieves all of them. In addition, the invention is not limited to achieving any of these purposes. Instead, as stated, a desired outcome is obtaining more accurate measurements than what was available in the past.

Figure 7A:
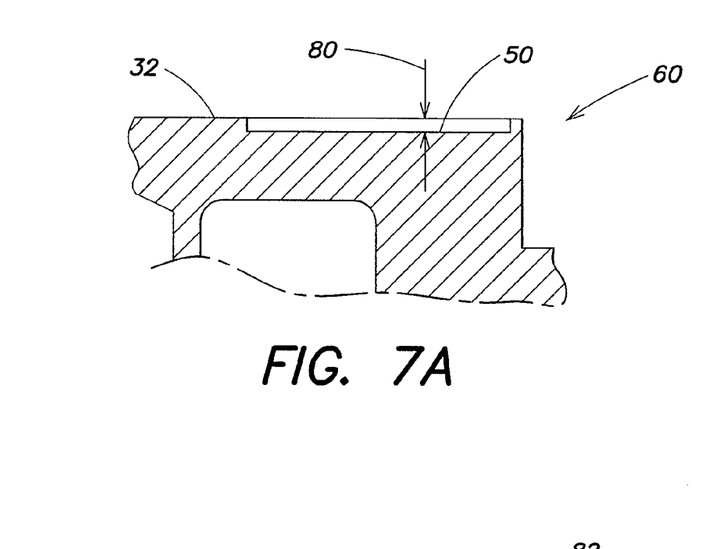
FIG. 7A is a cross-sectional view of the rheometer die taken along the line 7-7 in FIG. 3 according to one illustrative embodiment.
Figure 7B:
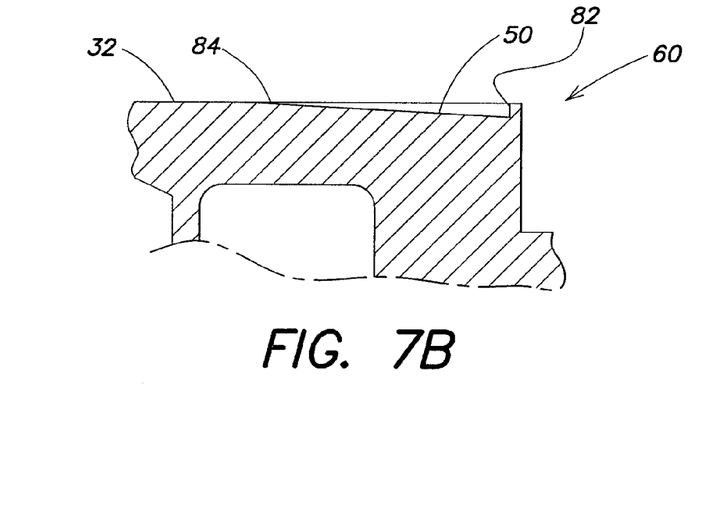
FIG. 7B is a cross-sectional view of the rheometer die taken along the line 7-7 in FIG. 3 according to another illustrative embodiment.

Turning to FIGS. 4, 7A and 7B, cross-sectional views of a rheometer die 60 are illustrated. As shown in FIG. 4, the surface 32 of the rheometer die 60 which contacts the material sample may be vertically offset from other portions of the rheometer die. As illustrated in the embodiment of FIG. 4, the thickness 80 of the two grooves 50 extending into the surface is substantially constant. FIG. 7A illustrates a more detailed view of the cross-sectional view of one groove 50 having a substantially constant thickness 80.

According to another embodiment illustrated in FIG. 7B, the groove thickness 80 into the surface 32 may vary from the first zone 52 to the second zone 56. For example, in one embodiment, a groove 50 may taper from a first end 82 in the first zone 52 adjacent the outer perimeter of the surface 32, to a second end 84 in the second zone 56. In this embodiment, the thickness 80 of the first end 82 of the groove 50 is greater than the thickness 80 of the second end 84 of the groove. It should be appreciated that in other embodiments, the thickness of the groove 50 may be arranged in other configurations, such as curved or stepped, as the present invention is not so limited. When a plurality of grooves 50 may extend into the rheometer surface 32, the thickness of the grooves 50 may differ from each other or alternatively, the grooves 50 may all have the same thickness 80.

In one illustrative embodiment, a rheometer die 60 may include a plurality of grooves 50. In particular, the embodiment illustrated in FIG. 3 includes 20 grooves. It should be appreciated that in other embodiments, a different number of grooves may extend into a rheometer die surface 32. It is also contemplated that the above-described grooves 50 may be positioned on a first moving rheometer die 14 and/or a second stationary rheometer die 12. In one embodiment, a plurality of grooves 50 are radially positioned about the center 70 of each rheometer die 12, 14. In this embodiment, the grooves 50 on each die may be substantially the same size and configuration, such that the second rheometer die 12 is constructed similar to the first rheometer die 14. In another embodiment, the grooves 50 on a rheometer surface may have different sizes and configurations and need not all be identical.

In one embodiment, the rheometer may be configured such that the grooves 50 on one die surface 32 are rotationally offset with the grooves 50 on the opposing die surface 32. When the grooves 50 are rotationally offset, the sample thickness may be more uniform throughout the chamber. In other embodiments, the grooves 50 on the opposing surfaces 32 may be in phase with each other. In one embodiment, a first set of grooves may be configured the same, but a second set of grooves may be configured differently from the first set of grooves.

It should be appreciated that the rheometer die 60 may be shaped in a variety of configurations, as the present invention is not limited in this respect. For example, as shown in the illustrative embodiments discussed above, one or more rheometer dies may have a substantially circular disk-shape and the rheometer surface 32 which forms a portion of the rheometer sample chamber may have a substantially planar plate-like configuration. In other embodiments, the one or more rheometer die surfaces 32 which form a portion of the rheometer sample chamber may have a substantially curved and/or conical shaped. In one embodiment, the above-described groove configuration may be used with a parallel plate rheometer which includes two substantially planar plate-like rheometer dies. In another embodiment, the above-described groove configuration may be used with a biconical rheometer which includes two substantially conical shaped rheometer dies. In yet another embodiment, the above-described groove configuration may be used with a cone and plate rheometer which includes one substantially planar plate-like rheometer die and one conical shaped rheometer die.

Figure 12:
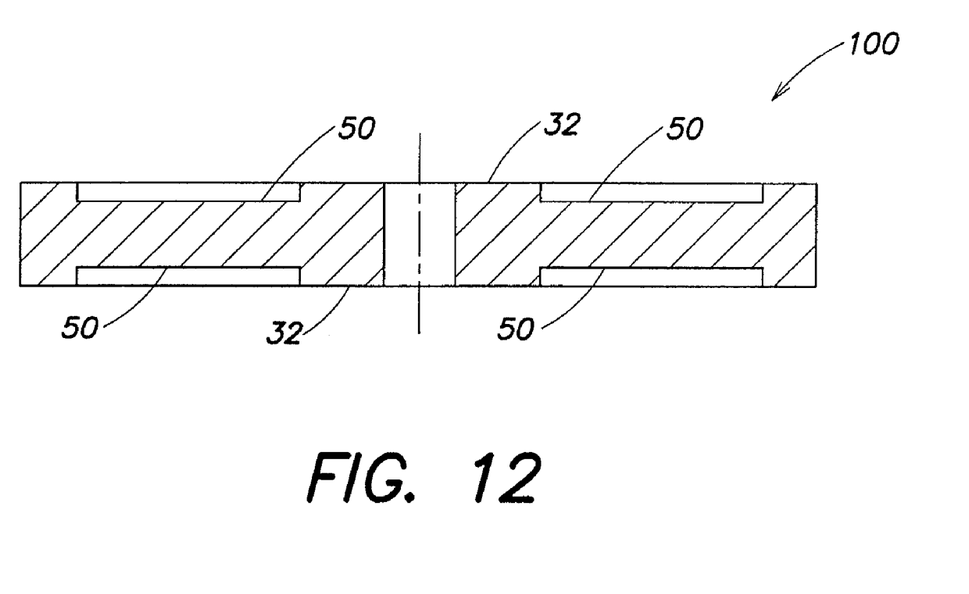
FIG. 12 is a cross-sectional view of a rheometer die according to one illustrative embodiment.

In one embodiment illustrated in FIG. 12, the rheometer die may be configured as a rheometer disk 100 adapted to be disposed within the test chamber. A rheometer disk 100 may be placed inside of the test chamber and a sample placed in the chamber may surround the rheometer disk 100. As illustrated in FIG. 12, the rheometer disk 100 may include one or more sample-contacting surfaces 32 which may include grooves 50 for reducing sample slippage in the rheometer chamber. The disk surfaces 32 may be substantially planar as shown. In another embodiment, the disk may be biconical shaped. The rheometer disk 100 may be configured to oscillate to exert a shear strain on the sample. In one embodiment, a rheometer which includes a rheometer disk 100 may be used to determine various curing or vulcanization characteristics of a sample, such as a rubber compound.

Figure 8:
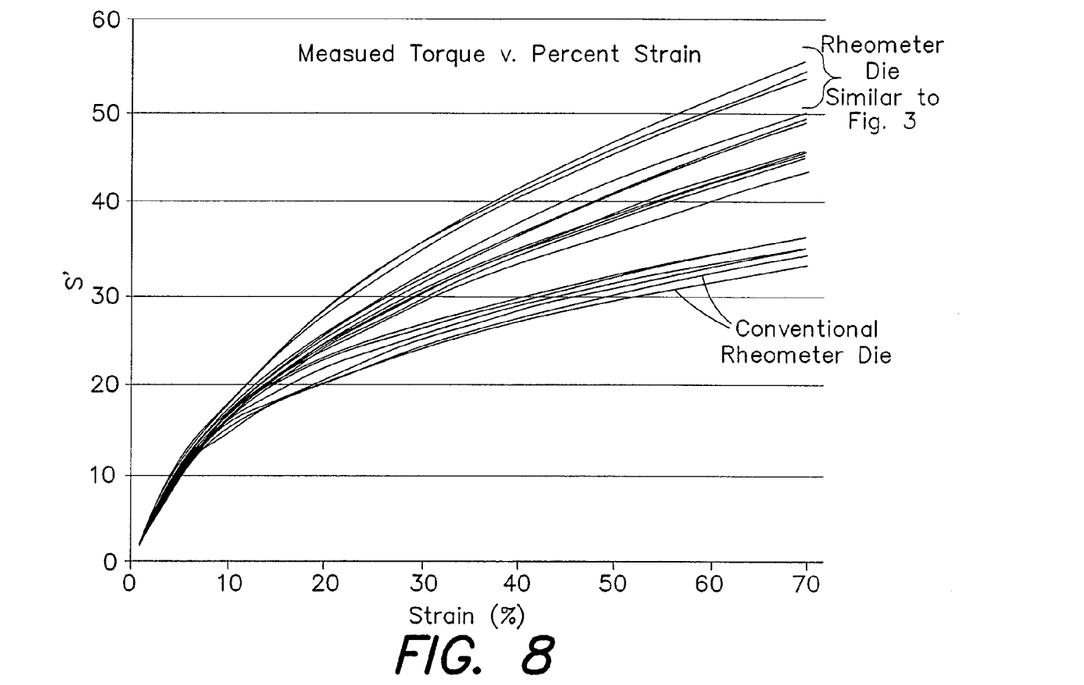
FIG. 8 is a graphical representation of the measured torque versus the percent strain according to several embodiments.
Figure 9:
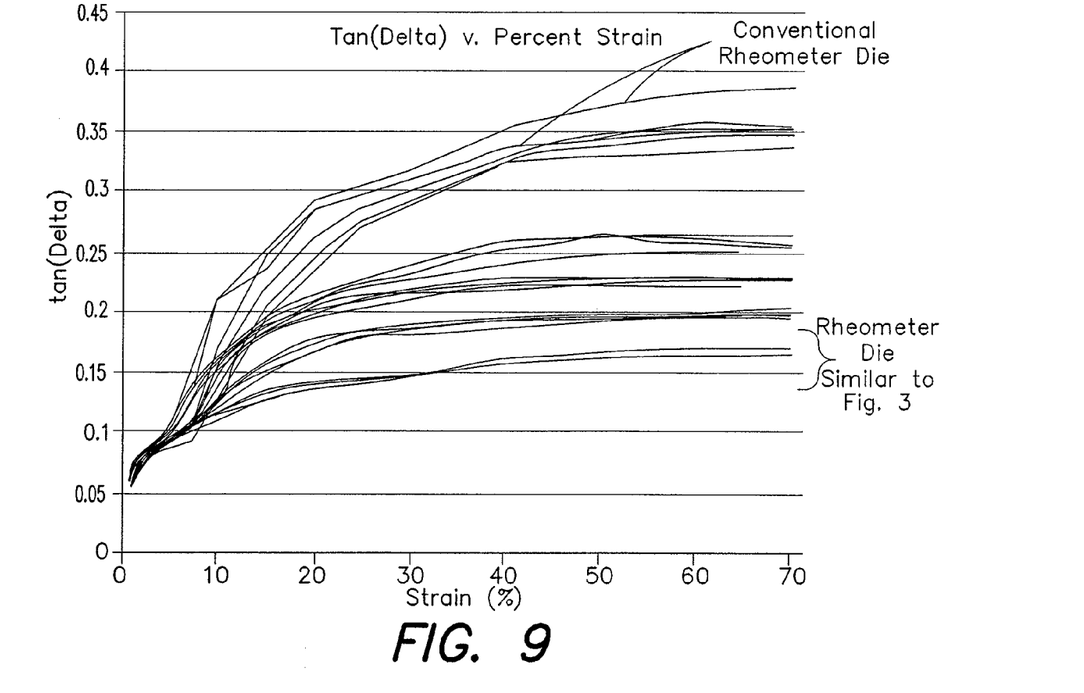
FIG. 9 is a graphical representation of tan(delta) versus the percent strain according to several embodiments.

As illustrated in FIGS. 8 and 9, experimental results indicate that a rheometer die according to certain embodiments of the present invention may reduce the amount of sample slippage in a rheometer chamber. For example, FIG. 8 is a graphical representation of the measured torque versus the percent strain for an elastomeric sample material where the torque is measured with a variety of rheometer die configurations according to different embodiments of the present invention. The graph in FIG. 8 may be known as a strain sweep. As a baseline, this data is compared to a conventional rheometer die configured similar to that illustrated in FIG. 1.

As shown in FIG. 8, at low strain percentages, such as at a 10% strain and lower, the different rheometer die designs result in relatively similar torque measurements. However, as the strain percentage on the elastomeric sample increases, the torque measured with the different rheometer dies begins to vary more substantially. For example, as shown, when the strain percentage is increased to approximately 50%, the conventional rheometer die design on FIG. 1 only measures a torque of approximately 30 dNM (deciNewton Meters). In contrast under approximately 50% strain, embodiments of the present invention measured torque between 35-45 dNM with the same elastomeric sample material. As shown in FIG. 8, in one embodiment of the present invention, when testing an elastomeric sample, the measured torque is at least 30 dNM when the strain percentage is approximately 30%. In another embodiment, when testing an elastomeric sample, the measured torque is at least 25 dNM when the strain percentage is approximately 25%.

As discussed above, at higher strains, as a sample material cools, it shrinks and may pull away from the rheometer die. This will produce a lower and inaccurate torque measurement. When the strain percentage is increased to approximately 70%, the conventional rheometer die design of FIG. 1 only measures a torque of approximately 33 dNM. However, at a similar stain percentage, embodiments of the present invention measure torque on the sample at approximately 42-55 dNM. This data illustrates that less sample slippage according to certain embodiments of the present invention may be obtained. As shown in FIG. 8, at higher strain percentages, such as at 20% strain and higher, certain embodiments of the present invention provide a measured torque which is greater than the measured torque provided by prior conventional rheometers. Therefore, according to certain embodiments of the present invention, accurate and repeatable torque measurements may be obtained at higher strain percentages.

FIG. 9 illustrates a graphical representation of tan(delta) versus the percent strain for a particular elastomeric sample material with a variety of rheometer die configurations according to different embodiments of the present invention. As a baseline, this data is also compared to a conventional rheometer die configured similar to that illustrated in FIG. 1.

Tan(delta) is a measure of the ratio between the viscous torque and the elastic torque for a particular sample material. A Fourier Transform of the torque and strain data may separate the measured torque into its elastic and viscous components to calculate tan(delta).

Tan(delta) is known to be a more sensitive indicator of slippage of a sample material in a rheometer. In general, the higher the tan(delta) value, the more the sample slippage. Also, a smooth curve with no discontinuity is generally an indication that the material sample has not slipped away from the rheometer surface. As illustrated in FIG. 9, the data for the conventional rheometer die design on FIG. 1 includes a bend or "knee" in the curve which indicates that the sample may have slipped away from the rheometer surface. As shown in FIG. 9, this is in contrast to the data for certain embodiments of the present invention which illustrate substantially smooth curves, even at higher strain percentages. As shown in FIG. 9, in one embodiment, when testing an elastomeric sample, the tan(delta) is less than 0.275 when the strain percentage is approximately 30%. In another embodiment, when testing an elastomeric sample, the tan(delta) is less than 0.32 when the strain percentage is approximately 40%. As shown in FIG. 9, at higher strain percentages, such as at 20% strain and higher, certain embodiments of the present invention provide a tan (delta) which is lower than the tan(delta) provided by prior conventional rheometer dies. This tan(delta) graph further illustrates that there may be less sample slippage according to certain embodiments of the present invention.

It should be appreciated that the dimensions associated with the above-described embodiments may vary depending upon the particular application. However, in one embodiment, the rheometer die has a total diameter of approximately 3 inches, where the diameter of the raised surface 32 which contacts the material sample is approximately 1.625 inches. In one embodiment, the overall radial length of a groove 50 is approximately between 0.4-0.6 inches and the groove thickness 80 may be approximately 0.03 inches and constant across the groove 50.

It should be appreciated that the rheometer die of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A rheometer die, comprising:
   a surface having a center; and
   at least one radial groove extending into the surface, the at least one groove defining at least a portion of a sample-holding chamber constructed and arranged to hold a sample, the at least one groove defining a first zone having sidewalls which taper generally towards the center, and a second zone with sidewalls which taper generally towards the center, the sidewalls of the first and second zones defining a transition region between the first zone and the second zone, at least one of the sidewalls having a non-linear portion defining the transition region.

2. The rheometer die of claim 1, wherein two sidewalls have a non-linear portion defining the transition region.

3. The rheometer die of claim 1, further comprising an upper portion and a spaced apart lower portion, wherein the upper and lower portions form at least an outer portion of the sample-holding chamber, and wherein the at least one groove extends into at least one of the upper and lower portions.

4. The rheometer die of claim 1, wherein the surface is substantially planar.

5. The rheometer die of claim 1, wherein the surface is substantially conical.

6. The rheometer die of claim 1, wherein the groove thickness tapers from a first end in the first zone adjacent the outer perimeter of the surface, to a second end in the second zone such that the thickness of the first end of the groove is greater than the thickness of the second end of the groove.

7. The rheometer die of claim 1, wherein the first zone is constructed and arranged such that imaginary extensions of the first zone sidewalls intersect before reaching the center.

8. The rheometer die of claim 1, wherein the second zone is constructed and arranged such that imaginary extensions of the second zone sidewalls intersect substantially at the center.

9. The rheometer die of claim 1, further comprising a disk-shaped element, wherein the at least one groove extends into the disk-shaped element.

10. The rheometer of claim 9, further comprising an upper portion and a spaced apart lower portion, wherein the upper and lower portions form at least an outer portion of the sample-holding chamber, and wherein the disk-shaped element is constructed and arranged to be positioned between the upper and lower portions.

11. The rheometer die of claim 1, wherein the at least one groove includes a plurality of grooves extending into the surface.

12. The rheometer die of claim 11, wherein each of the plurality of grooves define a first zone having sidewalls which taper generally towards the center, and a second zone with sidewalls which taper generally towards the center, the sidewalls of the first and second zones defining a transition region between the first zone and the second zone, at least one of the sidewalls having a non-linear portion defining the transition region.

13. The rheometer die of claim 11, wherein the outer periphery of the surface is substantially circular-shaped and the plurality of grooves are radially spaced apart along the surface.

14. A rheometer, comprising:
the rheometer die of claim 1 defining a first rheometer die;
a second rheometer die, the first and second rheometer dies defining the sample-holding chamber;
a drive mechanism constructed and arranged to rotate one rheometer die relative to the other rheometer die; and
a torque transducer constructed and arranged to measure the torque on the sample in the sample-holding chamber.

15. The rheometer of claim 14, wherein the first rheometer die is substantially planar.

16. The rheometer of claim 14, wherein the first rheometer die is substantially conical.

17. The rheometer of claim 14, wherein the second rheometer die is constructed and arranged similar to the first rheometer die.

18. The rheometer of claim 17, wherein the at least one groove on the first rheometer die is rotationally offset with the at least one groove on the second rheometer die.

19. A rheometer die, comprising:
a surface having a center; and
at least one radial groove extending into the surface, the at least one groove defining at least a portion of a sample-holding chamber constructed and arranged to hold a sample, wherein the at least one groove defines a first zone constructed and arranged to wedge a sample in the groove as the sample shrinks within the chamber upon cooling of the sample from a molten state to a solid state, and a second zone constructed and arranged such that as the sample shrinks, at least a portion of the sample located in the first zone moves into the second zone, the first and second zones defining a transition region therebetween, the transition region including an expansion area to accommodate movement of the sample into the second zone as the sample shrinks.

20. The rheometer die of claim 19, wherein the first zone has sidewalls which taper generally towards the center, and the second zone has sidewalls which taper generally towards the center, wherein the sidewalls of the second zone taper at a different angle than the sidewalls of the first zone.

21. The rheometer die of claim 19, wherein the transition region includes an expansion area on each side of the groove.

22. The rheometer die of claim 19, wherein the surface is substantially planar.

23. The rheometer die of claim 19, wherein the surface is substantially conical.

24. The rheometer die of claim 19, wherein the groove tapers from a first end in the first zone to a second end in the second zone such that the thickness of the first end of the groove is greater than the thickness of the second end of the groove.

25. The rheometer die of claim 19, wherein the first zone is constructed and arranged such that imaginary extensions of the first zone sidewalls intersect before reaching the center.

26. The rheometer die of claim 19, wherein the second zone is constructed and arranged such that imaginary extensions of the second zone sidewalls intersect substantially at the center.

27. The rheometer die of claim 19, further comprising an upper portion and a spaced apart lower portion, wherein the upper and lower portions form at least an outer portion of the sample-holding chamber, and wherein the at least one groove extends into at least one of the upper and lower portions.

28. A rheometer, comprising:
the rheometer die of claim 19 defining a first rheometer die;
a second rheometer die, the first and second rheometer dies defining the sample-holding chamber;
a drive mechanism constructed and arranged to move one rheometer die relative to the other rheometer die; and
a torque transducer constructed and arranged to measure the torque on the sample.

29. The rheometer die of claim 19, further comprising a disk-shaped element, wherein the at least one groove extends into the disk-shaped element.

30. The rheometer of claim 29, further comprising an upper portion and a spaced apart lower portion, wherein the upper and lower portions form at least an outer portion of the sample-holding chamber, and wherein the disk-shaped element is constructed and arranged to be positioned between the upper and lower portions.

31. The rheometer die of claim 19, wherein the at least one groove includes a plurality of grooves extending into the surface.

32. The rheometer die of claim 31, wherein each of the plurality of grooves defines a first zone constructed and arranged to wedge a sample in the groove as the sample shrinks, and a second zone constructed and arranged such that as the sample shrinks, at least a portion of the sample located in the first zone moves into the second zone, the first and second zones defining a transitional region therebetween, the transitional region including an expansion area to accommodate movement of the sample into the second zone.

33. The rheometer die of claim 31, wherein the outer periphery of the surface is substantially circular-shaped and the plurality of grooves are radially spaced apart along the surface.

34. A rheometer die, comprising:
a surface having a center; and
at least one radial groove extending into the surface, the at least one groove defining at least a portion of a sample-holding chamber constructed and arranged to hold a sample;
wherein the at least one groove defines a substantially wedge-shaped portion, the wedge-shaped portion having sidewalls which taper generally towards the center such that imaginary extensions of the sidewalls intersect before reaching the center.

35. The rheometer die of claim 34, wherein the at least one groove further comprises an expansion portion adjacent the wedge-shaped portion, the expansion portion having sidewalls which converge towards the center.

36. The rheometer die of claim 34, wherein the surface is substantially planar.

37. The rheometer die of claim 34, wherein the surface is substantially conical.

38. The rheometer die of claim 34, wherein the groove tapers from a first end in the first zone to a second end in the second zone such that the thickness of the first end of the groove is greater than the thickness of the second end of the groove.

39. The rheometer die of claim 34, further comprising an upper portion and a spaced apart lower portion, wherein the upper and lower portions form at least an outer portion of the sample-holding chamber, and wherein the at least one groove extends into at least one of the upper and lower portions.

40. A rheometer, comprising:
the rheometer die of claim 34 defining a first rheometer die;
a second rheometer die, the first and second rheometer dies defining the sample-holding chamber;
a drive mechanism constructed and arranged to move one rheometer die relative to the other rheometer die; and
a torque transducer constructed and arranged to measure the torque on the sample.

41. The rheometer die of claim 34, further comprising a disk-shaped element, wherein the at least one groove extends into the disk-shaped element.

42. The rheometer of claim 41, further comprising an upper portion and a spaced apart lower portion, wherein the upper and lower portions form at least an outer portion of the sample-holding chamber, and wherein the disk-shaped is constructed and arranged to be positioned between the upper and lower portions.

43. The rheometer of claim 35, wherein the expansion portion is constructed and arranged such that imaginary extensions of the expansion portion sidewalls intersect substantially at the center.

44. The rheometer die of claim 34, wherein the at least one groove includes a plurality of grooves extending into the surface.

45. The rheometer die of claim 44, wherein each of the plurality of grooves defines a substantially wedge-shaped portion, the wedge-shaped portion having sidewalls which converge towards the center such that imaginary extensions of the sidewalls intersect before reaching the center.

46. The rheometer die of claim 44, wherein the outer periphery of the surface is substantially circular-shaped and the plurality of grooves are radially spaced apart along the surface.

* * * * *